(12) United States Patent
Wu et al.

(10) Patent No.: US 7,801,264 B2
(45) Date of Patent: Sep. 21, 2010

(54) METHOD FOR CALIBRATING A DUAL-SPECTRAL COMPUTED TOMOGRAPHY (CT) SYSTEM

(75) Inventors: Xiaoye Wu, Rexford, NY (US); James Walter Leblanc, Niskayuna, NY (US); Paavana Sainath, Oconomowoc, WI (US)

(73) Assignee: General Electric Company, Niskayuna, NY (US)

( * ) Notice: Subject to any disclaimer, the term of this patent is extended or adjusted under 35 U.S.C. 154(b) by 245 days.

(21) Appl. No.: 11/959,709

(22) Filed: Dec. 19, 2007

(65) Prior Publication Data

US 2009/0161814 A1     Jun. 25, 2009

(51) Int. Cl.
*A61B 6/00*     (2006.01)
(52) U.S. Cl. .......................................................... 378/5
(58) Field of Classification Search ........................ 378/5
See application file for complete search history.

(56) References Cited

U.S. PATENT DOCUMENTS 4,789,930 A * 12/1988 Sones et al. ................. 378/207
5,155,365 A * 10/1992 Cann et al. ............... 250/363.02
6,574,302 B2 * 6/2003 Adriaansz ..................... 378/54
6,614,874 B2 * 9/2003 Avinash ........................ 378/62
6,845,142 B2 * 1/2005 Ohishi ............................ 378/8
6,987,833 B2 * 1/2006 Du et al. ..................... 378/98.9
7,086,780 B2   8/2006 Wu et al.

* cited by examiner

*Primary Examiner*—Edward J Glick
*Assistant Examiner*—Alexander H Taningco
(74) *Attorney, Agent, or Firm*—Jason K. Klindtworth (57) ABSTRACT

A method for calibrating and reconstructing material density images in a dual-spectral computed tomography (CT) system 100 is disclosed. An X-ray source in the CT system 100 emits a first X-ray spectrum and a second X-ray spectrum towards an object. The method includes computing calibration coefficients by using projection data from the object for the two X-ray spectra and by linearizing at least two basis materials such as bone and water simultaneously. Further, basis materials decomposition coefficients for the at least two basis materials are computed by linearizing the basis materials individually. Correction values for the projection data and for the basis materials are then computed by using the basis materials decomposition coefficients and the calibration coefficients. The computed correction values are used in reconstructing material density images for the basis materials.

20 Claims, 4 Drawing Sheets

METHOD FOR CALIBRATING A DUAL-SPECTRAL COMPUTED TOMOGRAPHY (CT) SYSTEM

BACKGROUND OF THE INVENTION

This invention relates generally to computed tomography (CT) systems, and more particularly to generating images in the computed tomography systems with reduced artifacts.

A CT system typically includes an X-ray source to project a beam of X-rays through an object, for example, a patient. The beam of X-rays projected towards the object gets attenuated after passing through the object. A detector array detects the attenuated X-ray beams from various angular positions with respect to the object and generates one or more signals. The signals are processed to obtain processed data, referred to as projection data. Further, the projection data are combined to reconstruct the object images, which represent the X-ray beams attenuation through the object. A spectral calibration can be performed on the detector elements to determine spectral response differences among the detector elements and to ensure that the reconstructed images are uniform and free of artifacts. Inaccurate determination of spectral response differences between detector elements due to, for example, beam hardening through water, soft-tissue, bone and contrast agents, and detector imperfection, results in rings and bands in images.

In a single-spectral CT system, the projection data for a given path is acquired with a single X-ray (or other radiation) spectrum. The spectral calibration is performed for each incident X-ray (or other radiation) spectrum to remove beam hardening and to correct the detector imperfection. A set of calibration coefficients are computed for the incident X-ray spectrum and a correction is expressed as a function of the calibration coefficients and the projection data from the same spectrum as, p_corr=f(c1, c2 . . . , p), where $c_1$, $c_2$ are the calibration coefficients and p is the projection data from the single spectrum. The spectral calibration method described above, linearizes the projection data to the length of a single basis material or to the length of basis materials having similar X-ray attenuation characteristics, for example, water and soft tissue. Hence, the spectral calibration with a single X-ray spectrum removes beam hardening artifacts due to a single material, such as water, when the incident beam is attenuated by water. In a dual-spectral CT system, the projection data for a given path is measured twice by using two X-ray spectra. Hence, a projection pair data set comprising projection data from the two X-ray spectra is obtained with the dual-spectral CT system.

Currently available methods for calibrating the dual-spectral CT system may employ the spectral calibration method of the single-spectral CT system as described above wherein calibration is performed at each of the two X-ray spectra for a single basis material. These methods therefore remove beam hardening and detector imperfection artifacts for a single basis material. However, such methods do not account for image artifacts due to other basis materials, for example, bone or other contrast agents. Therefore, there exists a need for calibrating a dual-spectral CT system, which will provide beam-hardening and detector-spectral artifact free images at more than one basis material.

BRIEF DESCRIPTION OF THE INVENTION

In an exemplary embodiment of the invention, a method for calibrating a computed tomography (CT) system is provided. The method includes acquiring detection coefficients for a plurality of detector elements of the CT system and computing calibration coefficients for a first X-ray spectrum and a second X-ray spectrum by linearizing at least two different basis materials, such as, bone and water simultaneously. The method further includes computing basis materials decomposition coefficients for the at least two different basis materials by linearizing the at least two different basis materials individually and using a projection pair data set. The calibration coefficients and the basis materials decomposition coefficients are employed in calibrating the CT system.

In another exemplary embodiment of the invention, a method for generating material density images in a computed tomography (CT) system is provided. The method includes measuring a projection pair data set having projection data from a first X-ray spectrum and a second X-ray spectrum and computing correction values for the projection pair data set using calibration coefficients for the first X-ray spectrum and the second X-ray spectrum, and the projection pair data set. The method further includes computing correction values for the at least two different basis materials by using basis materials decomposition coefficients for the at least two different basis materials, the projection pair data set and the correction values for the projection pair data set. The basis materials decomposition coefficients are calculated by linearizing the at least two different basis materials individually and by using the projection pair data set. Thereafter, material density images for each of the at least two different basis materials are reconstructed using the correction values.

In yet another embodiment of the invention a computed tomography (CT) system is provided. The CT system includes a gantry to receive an object to be scanned, an X-ray source within the gantry for emitting a plurality of distinct X-ray spectra and a detector array for generating one or more signals responsive to the plurality of distinct X-ray spectra and for measuring projection data. The CT system further includes a processor that is configured to compute correction values for a projection pair data set using calibration coefficients and the projection pair data set. The processor is further configured to compute correction values for the at least two different basis materials. Examples of the at least two different materials include, but are not limited to, water, soft tissue, bone and contrast agents. The at least two different materials have different X-ray attenuation characteristics. The processor is further configured to reconstruct material density images for the at least two different basis materials using the correction values for each of the at least two different basis materials.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

Various embodiments of the present invention provide a method and apparatus for calibrating and generating material density images in a computed tomography (CT) system, particularly a dual spectral CT system.

Figure 1:
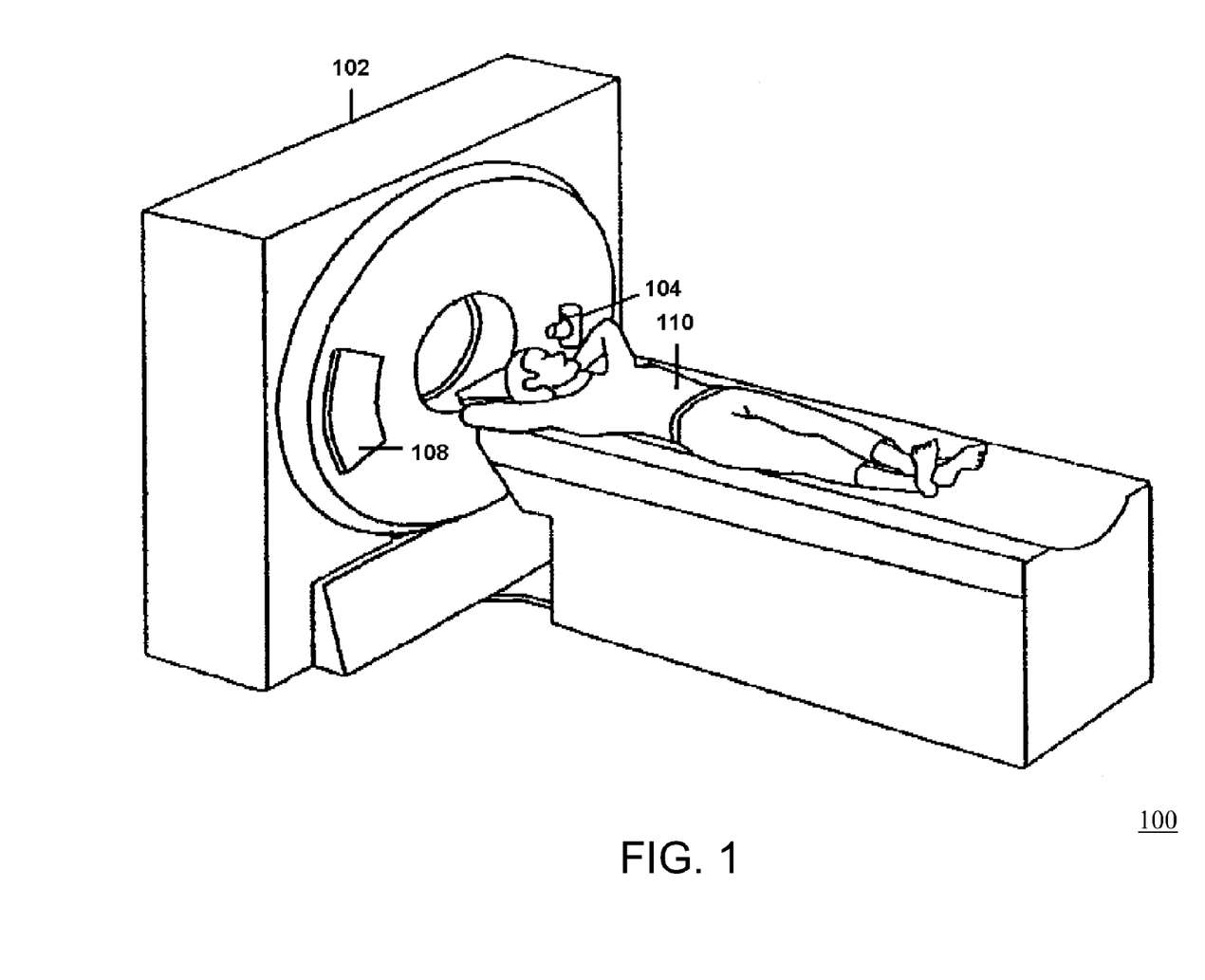
FIG. 1 illustrates a CT system in accordance with an exemplary embodiment of the invention.

FIG. 1 illustrates a computed tomography (CT) system 100, in accordance with an exemplary embodiment of the invention. The CT system 100 includes a gantry 102, an X-ray source 104 and a detector array 108. The gantry 102 controls the position of an object 110 to be inspected. The X-ray source 104 projects beams of X-rays towards the detector array 108. In an embodiment, the beams of X-rays may correspond to multiple X-ray spectra. The detector array 108 includes a plurality of detector elements (not shown) to detect the attenuated X-rays after passing through the object 110. The attenuation produced in the X-rays after passing through the object 110 is dependent on the length of basis materials, for example, water and bone, and attenuation characteristics of the basis materials through which the X-ray beam passes. The X-ray source 104 and the detector array 108 are rotated with the gantry 102 such that the angles at which the beams of X-rays intersect the object 110 constantly change. A single scan of the object 110 acquires X-ray attenuation measurements at one gantry angle, referred to as a view angle. In this embodiment, multiple scans of the object 110 at multiple view angles are obtained to acquire the X-ray attenuation measurements corresponding to the object 110.

In an embodiment, the X-ray source 104 projects a first X-ray spectrum and a second X-ray spectrum towards the detector array 108. Projection data $p_1$ from the first X-ray spectrum and projection data $p_2$ from the second X-ray spectrum represent attenuation produced by the X-ray beams from the two X-ray spectra after passing through the object 110. The dual projection pair data set $p_1$ and $p_2$ are used to calculate material density integrals using basis material decomposition calibration coefficients. These calibration coefficients and basis material decomposition coefficients linearize the at least two different basis materials such as bone and water simultaneously. The calibration coefficients and basis material decomposition coefficients are subsequently used to reconstruct images in the CT system 100 by using reconstruction techniques. Examples of reconstruction techniques include, but are not limited to, filtered back projection techniques. The method to calculate the calibration coefficients and the basis material decomposition coefficients is explained in conjunction with FIG. 3.

In one embodiment of the invention, the CT system 100 is a conventional CT system in which the detector and the X-ray source are positioned opposite one another and rotating with respect to one another. It will be apparent to those skilled in the art that the CT system 100 may be configured to have a stationary detector—rotating X-ray source configuration or a stationary detector and stationary X-ray source configuration. The two different basis materials have different X-ray attenuation characteristics. Examples of the at least two different basis materials include, but are not limited to, bone, water, soft tissue and contrast agents.

Figure 2:
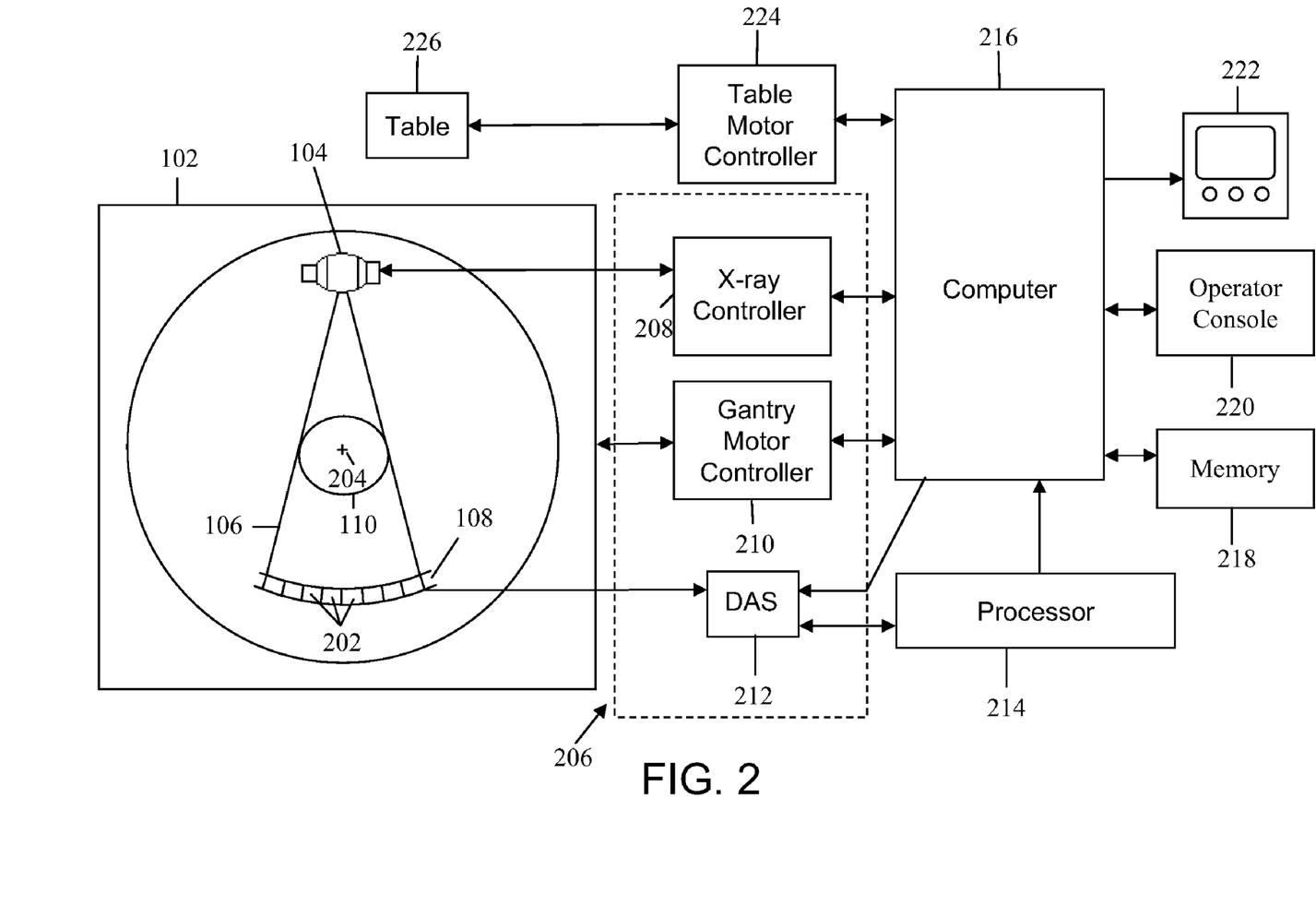
FIG. 2 is a block diagram representative of the CT system of FIG. 1.

FIG. 2 is a block diagram representative of the CT system 100 as described in FIG. 1. In the CT system 100, the X-ray source 104 and the detector array 108 are mounted on the gantry 102. The X-ray source 104 is configured to generate at least two X-ray spectra, and will be described in greater detail below. The detector array 108 includes a plurality of detector rows. Each detector row includes a plurality of detector elements 202 that detect the attenuated X-rays after passing through the object 110. In the illustrated embodiment, the CT system 100 includes a single row of the plurality of detector elements 202. In various embodiments of the invention, the detector array 108 may include a plurality of parallel rows of detector elements 202. The plurality of detector elements 202 produces signals based on the attenuation of the X-ray beams. The signals are used to estimate the attenuation of each X-ray beam 106 in the X-ray spectra. Further, the signals are processed to obtain projection data from the two spectra.

The gantry 102 and the components mounted therein rotate about a center of rotation 204 when a scan is performed to acquire the projection data from the object 110. The rotation of components on the gantry 102 and the operation of the X-ray source 104 are governed by a control mechanism 206 of the CT system 100. The control mechanism 206 includes an X-ray controller 208, a gantry motor controller 210 and a data acquisition system (DAS) 212. The X-ray controller 208 provides power and timing signals to the X-ray source 104. The gantry motor controller 210 controls the rotational speed and position of components on the gantry 102. The DAS 212 in the control mechanism 206 samples analog data from the detector elements 202 and converts the analog data to digital signals for further processing.

In an embodiment, the analog data can be the projection data $p_1$ and $p_2$. Further, a processor 214 receives sampled and digitized projection data from the DAS 212. The processor 214 is configured to compute calibration coefficients for the CT system 100 by using the detection coefficients and the projection data $p_1$ and $p_2$. The processor 214 is also configured to compute correction values for the projection data $p_1$ and $p_2$ and correction values for each of at least two different basis materials. In this exemplary embodiment, the at least two different basis materials have distinct X-ray attenuation characteristics. The processor 214 performs high-speed material density images reconstruction for each of the at least two different basis materials. Further, the reconstructed image quality depends on the accuracy of the X-ray projection signal, which is acquired by a two-dimensional array of detector pixels in the detector array 108. The detector pixels represent the attenuation of the basis materials. The reconstructed images are applied as an input to a computer 216. The reconstructed images are stored in a memory 218 of the computer 216. The memory 218 is also configured to store the calibration coefficients and the basis materials decomposition coefficients that are computed while calibrating the CT system 100. Examples of the memory 218 can be, but are not limited, to a Read-only memory (ROM).

The computer 216 may receive commands and scanning parameters from an operator via an operator console 220. In an embodiment, the operator console 220 may include a keyboard. A display 222 allows the operator to observe the reconstructed images and other data from the computer 216. Examples of the display 222 can be, but are not limited to, a cathode ray tube (CRT) display, liquid crystal display (LCD) and a plasma display. The operator supplied commands may be used by the computer 216 to provide control signals and information to control mechanism 206. In addition, the computer 216 may operate a table motor controller 224. The table motor controller 224 controls the movement of a table to position the object 110 in the gantry 102.

Particularly, the table moves the object 110 through a gantry opening. In an embodiment, the computer 216 includes a device for reading instructions and data from a computer-readable medium. Examples of the device can be, but are not limited to, a floppy disk drive, a CD-ROM drive, a DVD drive, a magnetic optical disk (MOD) device, or any other digital device including a network connecting device such as an Ethernet device. Examples of the computer-readable medium can be a floppy disk, a CD-ROM, a DVD or a digital source such as a network or the Internet, as well as yet to be developed digital means. In another embodiment, the computer 216 executes instructions stored in firmware (not shown). Examples of firmware include, but are not limited to, a basic input/output system (BIOS) built into the computer 216. The computer 216 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits.

In exemplary embodiments described herein, the X-ray source 104 is used to generate the first X-ray spectrum and the second X-ray spectrum. However, two distinct X-ray sources may be used to generate the first X-ray spectrum and the second X-ray spectrum. Further, although the herein described methods are described for a CT system, it is contemplated that the benefits of the invention accrue to imaging modalities other than CT. Moreover, although the herein described methods and apparatus are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

Figure 3:
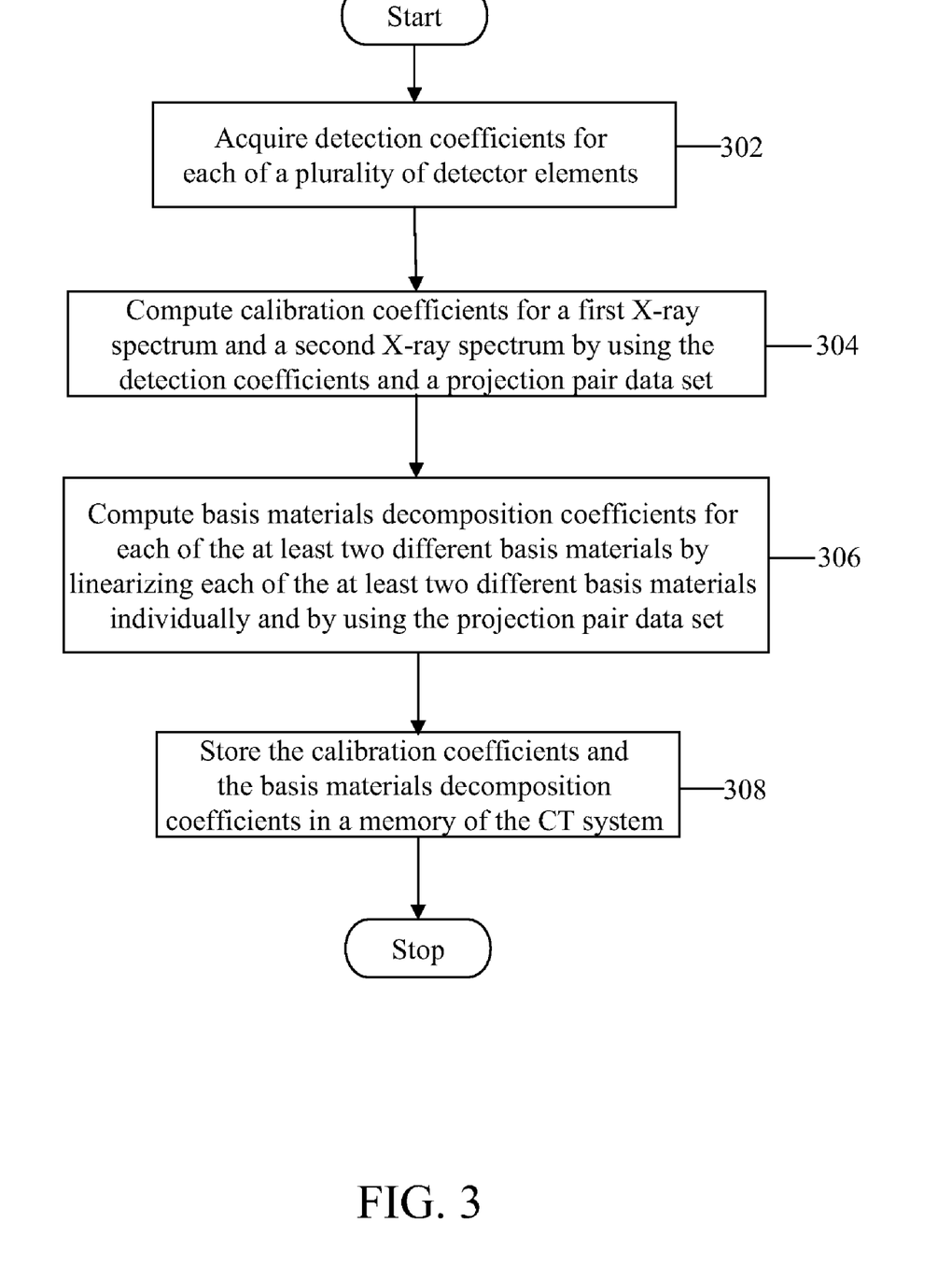
FIG. 3 is a flowchart illustrating a method for calibrating the CT system in accordance with an exemplary embodiment of the invention.

FIG. 3 is a flowchart illustrating a method for calibrating the CT system 100 in accordance with an exemplary embodiment of the invention. In an embodiment, the steps shown in the flowchart may be performed automatically by the computer 216 under a suitable program control. However, it is not required that the steps be performed in an automatic progression. In an embodiment, the program control is a firmware program, for example, the system basic input/output system (BIOS) built into the computer 216. In another embodiment, the program control is a device firmware program, for example, a device driver stored in the memory 218 of the CT system 100.

At step 302, the CT system 100 acquires detection coefficients f(E,i) for each of the plurality of detector elements 202 by measuring air scan data with two or more distinct X-ray spectra, for example, the first X-ray spectrum $S_1(E,i)$ and the second X-ray spectrum $S_2(E,i)$, or more air measurements at other incident spectra. Details of measurement of detection coefficients f(E, i) can be found in U.S. Pat. No. 7,086,780 entitled "Method for spectrally calibrating CT imaging apparatus detectors", assigned to the same assignee as this application, the entirety of which is hereby incorporated by reference herein. The first X-ray spectrum and the second X-ray spectrum are emitted, in an embodiment, by the X-ray source 104. The air scan data $A_1(i)$ and $A_2(i)$ with the incident X-ray spectra $S_1(E,i)$ and $S_2(E,i)$ is computed by using the following equations:

$$A_1(i) = \int S_1(E,i) \cdot E \cdot f(E,i) dE$$

$$A_2(i) = \int S_2(E,i) \cdot E \cdot f(E,i) dE \qquad (1)$$

where i is the detector pixel index formed by the CT system 100 and E is the incident photon energy.

The acquired detection coefficients f(E,i) are used to determine one or more signals detected by the plurality of detector elements 202 through air and through a given length of at least two different basis materials, for example, water and bone without physical measurements. A computed dataset through a given length of water $L_{water}$ and through a given length of bone $L_{bone}$ is computed using attenuation coefficients of the at least two different basis materials using the following equations:

$$WB_1(L_{water}, L_{bone}, i) = \int S_1(E,i) \cdot E \cdot f(E,i) e^{-\mu_w(E)L_{water} - \mu_b(E)L_{bone}} dE$$

$$WB_2(L_{water}, L_{bone}, i) = \int S_2(E,i) \cdot E \cdot f(E,i) e^{-\mu_w(E)L_{water} - \mu_b(E)L_{bone}} dE \qquad (2)$$

where $\mu_w$ and $\mu_b$ are the attenuation constants for water and bone respectively.

Accordingly, the projection data p1 and p2 at the first spectrum $S_1(E, i)$ and second spectrum $S_2(E, i)$ are obtained by using the air scan data $A_1(i)$, $A_2(i)$ from equation (1) and by using the measured dataset $WB_1$, $WB_2$ from equation (2) as:

$$p_1(L_{water}, L_{bone}, i) = -\log\left(\frac{\int S_1(E,i) \cdot E \cdot f(E,i) e^{-\mu_w(E)L_{water} - \mu_b(E)L_{bone}} dE}{\int S_1(E,i) \cdot E \cdot f(E,i) dE}\right)$$

$$p_2(L_{water}, L_{bone}, i) = -\log\left(\frac{\int S_2(E,i) \cdot E \cdot f(E,i) e^{-\mu_w(E)L_{water} - \mu_b(E)L_{bone}} dE}{\int S_2(E,i) \cdot E \cdot f(E,i) dE}\right) \qquad (3)$$

At step 304, calibration coefficients for the first X-ray spectrum $S_1(E, i)$ and the second X-ray spectrum $S_2(E, i)$ are computed by using the detection coefficients f(E,i) and projection pair data sets that include projection data $p_1$ from the first X-ray spectrum and projection data $p_2$ from the second X-ray spectrum. The calibration coefficients are computed by linearizing at least two different basis materials simultaneously. The at least two different basis materials have distinct X-ray attenuation characteristics. The linearization function $C_1$ is computed by using the projection pair data set $(p_1, p_2)$ in the following equation:

$$\mu_w L_{water} + \mu_b L_{bone} = C_1(p_1(L_{water}, L_{bone}, i), p_2(L_{water}, L_{bone}, i)) \qquad (4)$$

where $\mu_w$ and $\mu_b$ are the attenuation constants for water and bone respectively, $L_{water}$ and $L_{bone}$ are the length of water and bone respectively.

In an embodiment, the linearization function $C_1$ ( ) can be expressed as a polynomial function, for simplification, as:

$$\mu_w L_{water} + \mu_b L_{bone} = a_{10}^i p_1 + a_{01}^i p_2 + a_{20}^i p_1^2 + a_{11}^i p_1 p_2 + a_{02}^i p_2^2 + a_{30}^i p_1^3 + a_{21}^i p_1^2 p_2 + a_{12}^i p_1 p_2^2 + a_{03}^i p_2^3 + \ldots \qquad (5)$$

where the calibration coefficients a's are unknown and are obtained by fitting the projection pair data sets $(p_1, p_2)$ at various water length $(L_{water})$ and bone length $(L_{bone})$ values. With captured coefficients a's, the corrected projection is linearized to two materials simultaneously, eliminating beam hardening artifacts.

Thereafter, at step 306, basis materials decomposition coefficients for the two different basis materials are computed by linearizing each of the at least two different basis materials individually and by using the projection pair data set $(p_1, p_2)$.

The at least two different basis materials, water and bone are linearized individually by using the following equations:

$$L_{water} = C_w(p_1(L_{water}, L_{bone}, i), p_2(L_{water}, L_{bone}, i))$$

$$L_{bone} = C_w(p_1(L_{water}, L_{bone}, i), p_2(L_{water}, L_{bone}, i)) \quad (6)$$

where $C_w()$ and $C_b()$ are the basis materials decomposition functions for the basis materials, water and bone.

In an embodiment, the functions $C_w()$ and $C_b()$ are expressed as polynomial functions:

$$L_{water} = A_{10}^i p_1 + A_{01}^i p_2 + A_{20}^i p_1^2 + A_{11}^i p_1 p_2 + A_{02}^i p_2^2 + A_{30}^i p_1^3 + A_{21}^i p_1^2 p_2 + A_{12}^i p_1 p_2^2 + A_{03}^i p_2^3 + \ldots$$

$$L_{bone} = B_{10}^i p_1 + B_{01}^i p_2 B_{20}^i p_1^2 + B_{11}^i p_1 p_2 + B_{02}^i p_2^2 + B_{30}^i p_1^3 + B_{21}^i p_1^2 p_2 + B_{12}^i p_1 p_2^2 + B_{03}^i p_2^3 + \ldots \quad (7)$$

where the basis materials decomposition coefficients A's and B's for water and bone respectively are computed by fitting the projection pair data set $(p_1, p_2)$.

The calibration coefficients a's and the basis materials decomposition coefficients A's and B's computed above are stored in the memory 218 of the CT system 100. The calibration coefficients a's and the basis materials decomposition coefficients A's and B's are employed in calibrating the CT system 100.

Figure 4:
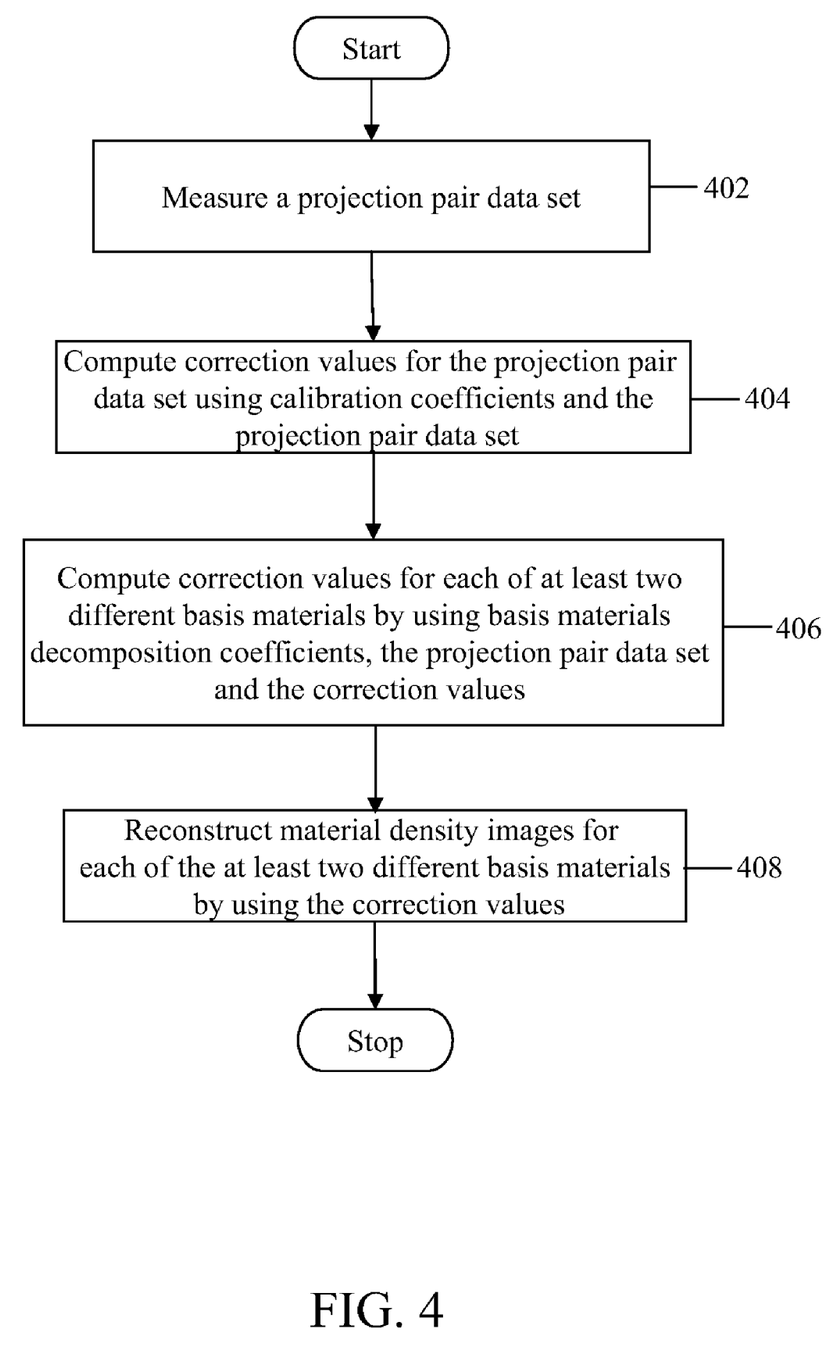
FIG. 4 is a flowchart illustrating a method for generating material density images in the CT system in accordance with an exemplary embodiment of the invention.

FIG. 4 is a flowchart illustrating a method for generating material density images in the CT system 100 in accordance with an exemplary embodiment of the invention. At step 402, a projection pair data set $(\tilde{p}_1, \tilde{p}_2)$ from the first X-ray spectrum and the second X-ray spectrum is measured. At step 404, the correction values for the projection pair data set $(\tilde{p}_1, \tilde{p}_2)$ are computed using the calibration coefficients a's (from equation (5)) and the projection pair data set $(\tilde{p}_1, \tilde{p}_2)$. The correction value $\tilde{p}_{corr}$ for each detector pixel is expressed as a polynomial function of the projection pair data $(\tilde{p}_1, \tilde{p}_2)$ and the calibration coefficients a's. The correction value $\tilde{p}_{corr}$ is computed for each detector pixel by using the equation:

$$\tilde{p}_{corr} = a_{10}^i \tilde{p}_1 + a_{01}^i \tilde{p}_2 + a_{20}^i \tilde{p}_1^2 + a_{11}^i \tilde{p}_1 \tilde{p}_2 + a_{02}^i \tilde{p}_2^2 + a_{30}^i \tilde{p}_1^3 + a_{21}^i \tilde{p}_1^2 \tilde{p}_2 + a_{12}^i \tilde{p}_1 \tilde{p}_2^2 + a_{03}^i \tilde{p}_2^3 + \ldots \quad (8)$$

Thereafter, at step 406, correction values for each of at least two different basis materials are computed by using the basis materials decomposition coefficients A's and B's, the projection pair data set $(\tilde{p}_1, \tilde{p}_2)$. The correction values representing material density line integral for the two basis materials, water and bone are computed using the following equations:

$$\tilde{p}_{water} = A_{10}^i \tilde{p}_1 + A_{01}^i \tilde{p}_2 + A_{20}^i \tilde{p}_1^2 + A_{11}^i \tilde{p}_1 \tilde{p}_2 + A_{02}^i \tilde{p}_2^2 + A_{30}^i \tilde{p}_1^3 + A_{21}^i \tilde{p}_1^2 \tilde{p}_2 + A_{12}^i \tilde{p}_1 \tilde{p}_2^2 + A_{03}^i \tilde{p}_2^3 + \ldots$$

$$\tilde{p}_{bone} = B_{10}^i \tilde{p}_1 + B_{01}^i \tilde{p}_2 + B_{20}^i \tilde{p}_1^2 + B_{11}^i \tilde{p}_1 \tilde{p}_2 + B_{02}^i \tilde{p}_2^2 + B_{30}^i \tilde{p}_1^3 + B_{21}^i \tilde{p}_1^2 \tilde{p}_2 + B_{12}^i \tilde{p}_1 \tilde{p}_2^2 + B_{03}^i \tilde{p}_2^3 + \ldots \quad (9)$$

The basis materials decomposition coefficients A's and B's, are obtained for each detector pixel from the first X-ray spectrum and the second X-ray spectrum for each detector pixel. The coefficients A's and B's also represent detector response of each detector pixel to incident photons. Since the basis materials decomposition coefficients A's and B's are obtained for each detector pixel, and the detector response of each detector pixel, the above equation not only provides accurate correction values for each of the at least two different basis materials, water and bone, but also removes detector imperfection. At step 408, material density images for each of the at least two different basis materials, water and bone are reconstructed by using the correction values $\tilde{p}_{water}$, $\tilde{p}_{bone}$. Hence, the reconstructed material density images account for beam hardening effects for the at least two different basis materials, water and bone, and any other material that can be decomposed into water and bone.

Various embodiments of the invention provide a calibration and correction method of a CT system that acquires information on the object and the detector array by using a first X-ray spectrum and a second X-ray spectrum. The CT system uses this information for computing correction values that are used for reconstructing material density images for at least two different basis materials with different X-ray attenuation characteristics. The method facilitates linearization of the at least two different basis materials. Hence, the reconstructed images have improved quality and resolution due to the removal of artifacts caused by the at least two different basis materials. Further, the method facilitates calibration of the CT system without the need of complex phantom measurements.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for calibrating a computed tomography (CT) system, the method comprising:
   acquiring detection coefficients for a plurality of detector elements of the CT system;
   computing by at least one processor, calibration coefficients for a first X-ray spectrum and a second X-ray spectrum using the detection coefficients and computed projection pair data sets by linearizing at least two different basis materials simultaneously;
   computing by the at least one processor, basis materials decomposition coefficients for each of the at least two different basis materials by linearizing each of the at least two different basis materials individually and using the computed projection pair data sets; and
   wherein the calibration coefficients and the basis materials decomposition coefficients are employed in calibrating the CT system.

2. The method of claim 1, wherein acquiring the detection coefficients comprises measuring air scan data with two or more incident X-ray spectra.

3. The method of claim 1, wherein the projection pair data sets comprise projection data from the first X-ray spectrum and the second X-ray spectrum.

4. The method of claim 3 further comprising calculating the projection data based on air scan data and attenuation coefficients of the at least two different basis materials.

5. The method of claim 1 further comprising storing the calibration coefficients and the basis materials decomposition coefficients in a memory of the CT system.

6. The method of claim 1 wherein the at least two different basis materials have distinct X-ray attenuation characteristics.

7. The method of claim 1, wherein the at least two different basis materials comprise at least two of bone, water, soft-tissue and contrast agent.

8. A method performed by at least one processor for generating material density images in a computed tomography (CT) system, the method comprising:
   computing by the at least one processor, a projection pair data set having projection data from a first X-ray spectrum and a second X-ray spectrum;
   computing by the at least one processor, correction values for the projection pair data set using calibration coefficients for the first X-ray spectrum and the second X-ray spectrum, and the projection pair data set;

computing by the at least one processor, correction values for each of at least two different basis materials using basis materials decomposition coefficients for each of the at least two different basis materials, the projection pair data set and the correction values, the basis materials decomposition coefficients being computed by linearizing each of the at least two different basis materials individually and using the projection pair data set; and reconstructing by the at least one processor, material density images for each of the at least two different basis materials using the correction values for each of the at least two different basis materials.

9. The method of claim 8 further comprising computing the calibration coefficients using detection coefficients and the projection pair data set.

10. The method of claim 8 further comprising calculating the projection data based on air scan data and attenuation coefficients of the at least two different basis materials.

11. The method of claim 8, wherein the correction values are computed using polynomial functions of the projection pair data set and the calibration coefficients.

12. The method of claim 8, wherein the at least two different basis materials have distinct X-ray attenuation characteristics.

13. The method of claim 8, wherein the at least two different basis materials comprise at least two of bone, water, soft-tissue and contrast agent.

14. A computed tomography (CT) system comprising:

a gantry to receive an object to be scanned;

an X-ray source within the gantry for emitting a plurality of distinct X-ray spectra;

a detector array comprising a plurality of detector elements for generating one or more signals responsive to the plurality of distinct X-ray spectra and for measuring projection pair data; and a processor configured to:

compute correction values for a projection pair data set using calibration coefficients for a first X-ray spectrum and a second X-ray spectrum and the projection pair data set;

compute correction values for each of at least two different basis materials using basis materials decomposition coefficients for each of the at least two different basis materials, the projection pair data set and the correction values, the basis materials decomposition coefficients being computed by linearizing each of the at least two different basis materials individually and by using the projection pair data set; and reconstruct material density images for each of the at least two different basis materials using the correction values for each of the at least two different basis materials.

15. The CT system of claim 14, wherein the processor is further configured to compute calibration coefficients using detection coefficients of the plurality of detector elements and the projection pair data set.

16. The CT system of claim 14, wherein the projection pair data set comprises projection data from the first X-ray spectrum and the second X-ray spectrum.

17. The CT system of claim 16, wherein the projection data are calculated based on air scan data and attenuation coefficients of the at least two different basis materials.

18. The CT system of claim 14, wherein the at least two different basis materials have distinct X-ray attenuation characteristics.

19. The CT system of claim 14, wherein the at least two different basis materials comprise at least two of bone, water, soft-tissue and contrast agent.

20. The CT system of claim 14, further comprising a memory for storing the calibration coefficients and the basis materials decomposition coefficients.

* * * * *

UNITED STATES PATENT AND TRADEMARK OFFICE
CERTIFICATE OF CORRECTION

PATENT NO. : 7,801,264 B2
APPLICATION NO. : 11/959709
DATED : September 21, 2010
INVENTOR(S) : Wu et al.

It is certified that error appears in the above-identified patent and that said Letters Patent is hereby corrected as shown below:

In Column 1, Line 36, delete "(c1, c2 ..., p)," and insert -- $(c_1, c_2 ..., p)$, --, therefor.

In Column 6, Lines 8-9, in Equation (2), delete " $\mu_b(E) L^{bone} dE$ " and insert -- $\mu_b(E) L_{bone} dE$ --, therefor.

In Column 6, Lines 11-12, in Equation (2), delete " $\mu_b(E) L^{bone} dE$ " and insert -- $\mu_b(E) L_{bone} dE$ --, therefor.

In Column 6, Line 16, delete "p1 and p2" and insert -- $p_1$ and $p_2$ --, therefor.

In Column 7, Line 5, in Equation (6), delete "$C_w$" and insert -- $C_b$ --, therefor.

In Column 7, Line 50, in Equation (9), delete " $B_{12}{}^i \tilde{p}_1 \tilde{p}_1{}^2$ " and insert -- $B_{12}{}^i \tilde{p}_1 \tilde{p}_2{}^2$ --, therefor.

Signed and Sealed this

Sixteenth Day of November, 2010

David J. Kappos
*Director of the United States Patent and Trademark Office*